(12) United States Patent
Groszmann et al.

(10) Patent No.: US 8,694,075 B2
(45) Date of Patent: Apr. 8, 2014

(54) INTRA-OPERATIVE REGISTRATION FOR NAVIGATED SURGICAL PROCEDURES

(75) Inventors: Daniel Eduardo Groszmann, Cambridge, MA (US); Vernon Thomas Jensen, Draper, UT (US); Vianney Pierre Battle, Paris (FR)

(73) Assignee: General Electric Company, Schenectady, NY (US)

( * ) Notice: Subject to any disclaimer, the term of this patent is extended or adjusted under 35 U.S.C. 154(b) by 1142 days.

(21) Appl. No.: 12/643,824

(22) Filed: Dec. 21, 2009

(65) Prior Publication Data

US 2011/0152676 A1 Jun. 23, 2011

(51) Int. Cl.
*A61B 5/05* (2006.01)

(52) U.S. Cl.
USPC ........... 600/426; 600/427; 600/429; 606/130; 382/128

(58) Field of Classification Search
None
See application file for complete search history.

(56) References Cited

U.S. PATENT DOCUMENTS

| | | | |
|---|---|---|---|
| 4,791,934 A | 12/1988 | Brunnett | |
| 6,175,614 B1 | 1/2001 | Jensen et al. | |
| 6,484,049 B1 | 11/2002 | Seeley et al. | |
| 6,490,475 B1 | 12/2002 | Seeley et al. | |
| 6,666,579 B2 | 12/2003 | Jensen | |
| 6,714,629 B2 | 3/2004 | Vilsmeier | |
| 6,771,736 B2 | 8/2004 | Sabol et al. | |
| 6,814,489 B2 | 11/2004 | Jensen et al. | |
| 6,823,207 B1 | 11/2004 | Jensen et al. | |
| 6,885,724 B2 | 4/2005 | Li et al. | |
| 6,944,265 B2 | 9/2005 | Warp et al. | |
| 7,117,027 B2 | 10/2006 | Zheng et al. | |
| 7,139,417 B2 | 11/2006 | Nicolas et al. | |
| 7,177,455 B2 | 2/2007 | Warp et al. | |
| 7,184,062 B2 | 2/2007 | Battle | |
| 7,369,695 B2 | 5/2008 | Zettel et al. | |
| 7,412,111 B2 | 8/2008 | Battle et al. | |
| D580,286 S | 11/2008 | Groszmann et al. | |
| 7,492,931 B2 | 2/2009 | Sabol et al. | |
| 7,522,701 B2 | 4/2009 | Jensen et al. | |
| 7,603,155 B2 | 10/2009 | Jensen | |
| 2001/0036245 A1 | 11/2001 | Kienzle et al. | |
| 2002/0085681 A1* | 7/2002 | Jensen | 378/197 |
| 2004/0015077 A1 | 1/2004 | Sati et al. | |
| 2004/0076259 A1 | 4/2004 | Jensen et al. | |
| 2005/0084147 A1 | 4/2005 | Groszmann | |

(Continued)

FOREIGN PATENT DOCUMENTS

| | | |
|---|---|---|
| EP | 1 173 105 | 1/2002 |
| EP | 1 593 343 | 9/2005 |

OTHER PUBLICATIONS

Daly et al. Geometric calibration of a mobile C-arm for intraoperative cone-beam CT. Medical Physics, vol. 35 No. 5, 2124-2136, May 2008.

(Continued)

*Primary Examiner* — Parikha Mehta
(74) *Attorney, Agent, or Firm* — Fletcher Yoder, P.C.

(57) ABSTRACT

A navigation system for use during a surgical procedure is provided. The navigation system is configured to use electromagnetic tracking data produced by electromagnetic tracking devices and 2D image data produced by a fluoroscope to intra-operatively register 2D images of a patient to a pre-operative 3D image of the patient. In some implementations, a surgeon may be able to perform an interventional or surgical procedure guided by the navigation system.

14 Claims, 7 Drawing Sheets

(56) References Cited

U.S. PATENT DOCUMENTS

| | | |
|---|---|---|
| 2005/0169510 A1 | 8/2005 | Zuhars et al. |
| 2006/0061570 A1 | 3/2006 | Cheryauka et al. |
| 2007/0129629 A1 | 6/2007 | Beauregard et al. |
| 2007/0167744 A1 | 7/2007 | Beauregard et al. |
| 2007/0211927 A1 | 9/2007 | Groszmann et al. |
| 2008/0004523 A1 | 1/2008 | Jensen |
| 2008/0118103 A1 | 5/2008 | Pescatore et al. |
| 2008/0125997 A1 | 5/2008 | Li et al. |
| 2008/0154526 A1 | 6/2008 | Li et al. |
| 2008/0161679 A1 | 7/2008 | von Jako et al. |
| 2008/0204000 A1 | 8/2008 | Groszmann et al. |
| 2008/0287778 A1 | 11/2008 | Li et al. |
| 2008/0287803 A1* | 11/2008 | Li et al. .......... 600/466 |
| 2008/0300481 A1 | 12/2008 | Groszmann et al. |
| 2008/0314973 A1 | 12/2008 | Zuhars et al. |
| 2009/0080737 A1 | 3/2009 | Battle et al. |
| 2009/0088629 A1 | 4/2009 | Groszmann et al. |

OTHER PUBLICATIONS

Bebis, Geometry of Perspective Projection. Computer Science Department.CS491E/791E:Computer Vision (Spring 2004).

\* cited by examiner

//INTRA-OPERATIVE REGISTRATION FOR NAVIGATED SURGICAL PROCEDURES

BACKGROUND OF THE INVENTION

The present technique relates generally to interventional and surgical medical procedures. In particular, the present technique relates to image-guided therapy techniques, such as those used in conjunction with various surgical or radiological procedures.

As medical imaging technologies have matured, it has become possible to combine the use of medical imaging techniques with the performance of invasive procedures. For example, interventional procedures such as biopsies and tumor ablations may benefit from the use of imaging techniques that allow a clinician to visualize the target region along with the intervention device while the procedure is being performed. In this way, the clinician may guide the interventional device to the target region with relative accuracy, low reliance on continuous x-ray updates and, perhaps, without unnecessary tissue damage.

In general, an image may be displayed on a monitor to provide position information to an operator, such as a clinician. The image may include a visualization of the patient's anatomy along with a graphical representation of the interventional or surgical device. As the device is positioned with respect to the patient's body, the displayed image is updated to reflect the correct device coordinates. The base image of the patient's anatomy may be generated either prior to or during the medical procedure. For example, any suitable medical imaging technique, such as X-ray, computed tomography (CT), magnetic resonance imaging (MRI), positron emission tomography (PET), single positron emission computed tomography (SPECT) and ultrasound, may be utilized to provide the base image displayed during tracking. The combination of the base image and the representation of the tracked device provides positioning information that allows a medical practitioner to manipulate a device to a desired position and/or associate information gathered to a precise location.

In practice, such image-guided therapy techniques typically employ a tracking frame of reference device placed proximate to the anatomy of interest. The reference device moves with the patient to provide accurate and consistent tracking of the anatomy of interest. Such image-based navigation systems typically perform a registration to align the coordinate system of the medical image to the tracking device. For example, traditional registration methods require the operator to identify anatomical or fiducial locations on the patient (e.g., point-pair, skin or tissue surface, and the like). For some procedures, this process can be time consuming, laborious, and the accuracy can be insufficient due to the user variability involved. For minimally invasive surgical (MIS) procedures, especially in the spine, there is a further limitation in that the anatomy of interest is not easily accessible for point-pair or surface registration methods.

BRIEF DESCRIPTION OF THE INVENTION

The present technique is generally directed to the dynamic referencing of an internal structure in an image-guided surgical procedure. In one implementation, three or more sensor elements are provided. In such an embodiment, at least one of the sensor elements is attached to an internal structure, such as bone. Other sensor elements are attached to a C-arm of a fluoroscope and an interventional device, such as a surgical tool. Signals or fields generated and received by the sensor elements, such as electromagnetic signals or fields, may be used to determine the positions and orientations of the sensor elements with respect to each other. The positions and orientations of the sensor elements may then be registered with a set of 3D scan based data (such as CT, MRI, PET, SPECT), which may have been taken prior to the surgical procedure. In one embodiment, the registration occurs by taking two initial fluoroscopic (fluoro) images and registering the fluoroscopic images to the sensor elements in the C-arm, followed by registering the fluoroscopic images and measured fluoroscope position and orientation data with the 3D scan. Once the positions and orientations of the C-arm sensor elements are registered with the 3D scan of the internal structure, any updates to the position and orientation information derived from the sensor elements may be used to modify or adjust the visual representation of the surgical tool with respect to the 3D scan of the internal structure. The modified or adjusted visual representation of the surgical tool may then be used to allow a surgeon or other clinician to perform an image-guided invasive procedure based on images reflecting the current position and shape of the internal structure.

In accordance with one aspect of the present technique, a surgical navigation method is provided. In accordance with this method, a three-dimensional representation of a region of interest of a patient is acquired resulting in a three-dimensional image dataset. The image dataset contains the images and the associated coordinate system of the images. A patient coordinate frame is established based on the position and orientation of a first electromagnetic device attached to the patient. Two or more two-dimensional fluoroscopic images of the patient are acquired. The position and orientation of the C-arm in the patient coordinate frame is measured for each of the fluoroscopic images by a second electromagnetic device attached to the C-arm. At least two of the fluoroscopic images are at generally orthogonal angles to one another. The three-dimensional images and associated image coordinates, the two or more two-dimensional fluoroscopic images, and the position and orientation of the C-arm in the patient coordinate frame for each of the fluoroscopic images, are provided to a computerized navigation system. The two or more two-dimensional fluoroscopic images are mapped to the patient coordinate frame. In addition, the two or more two-dimensional fluoroscopic images are registered to the three dimensional representation of the region of interest to produce a navigable three-dimensional visualization of the patient.

In accordance with one aspect of the present technique, a method of surgical navigation is provided. In accordance with this method, a first electromagnetic device is attached to a patient anatomy of interest, such that the first electromagnetic device establishes a patient coordinate frame. Two or more fluoroscopic images are acquired using a C-arm imaging system. The C-arm imaging system comprises a second electromagnetic device and a calibration target. A registration operation is performed using a computerized navigation system configured to process the patient coordinate frame, the two or more fluoroscopic images, calibration data derived based upon the calibration target and location of the C-arm electromagnetic device, position and orientation data derived for the C-arm using the second electromagnetic device, and a three-dimensional image dataset of the patient anatomy of interest generated prior to surgery. The surgical tool is equipped with a third electromagnetic device. A representation of a surgical tool depicted with respect to the three-dimensional representation of the patient is displayed using the registration operation.

In accordance with one aspect of the present technique, a surgical navigation system is provided. The surgical navigation system includes an interface unit configured to receive electromagnetic tracking data produced by one or more electromagnetic tracking devices and an interface unit configured to receive the two-dimensional fluoroscopic images. The system also includes a memory configured to store the two-dimensional fluoroscopic images, the electromagnetic tracking data, and a three-dimensional image of the patient. In addition, the system includes processing circuitry configured to execute one or more algorithms for registering the two-dimensional fluoroscopic images to the three-dimensional image and for generating a representation based on the registered two-dimensional fluoroscopic images and the three-dimensional image. The system also includes a workstation in communication with the processing circuitry configured to communicate with a user interface and a display.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

The present technique is directed to dynamic referencing and registration of images to patient anatomy for image-guided surgical and interventional procedures. In particular, the present technique utilizes electromagnetic (EM) tracking devices attached to each of a C-arm fluoroscope, an interventional device, and a patient. The EM tracking devices attached to the patient are configured for attachment to an anatomy of interest such that movement of the anatomy can be tracked in conjunction with acquired images or image data. In particular, in one embodiment, a surgical navigation system using electromagnetic tracking technology integrated into a fluoroscopic C-arm is used to register intra-operatively to a pre-operative CT scan of the patient. The C-arm is used to take at least 2 initial fluoroscopic images of the patient's anatomy of interest. This image data, together with the EM data of the C-arm pose (i.e., position and orientation) with respect to the patient's anatomy, is used to allow navigation using a pre-operative CT scan or other 3D medical scan such as MRI, PET, SPECT, and the like. The registration can be updated throughout the procedure if necessary by taking additional fluoroscopic images.

Figure 1:
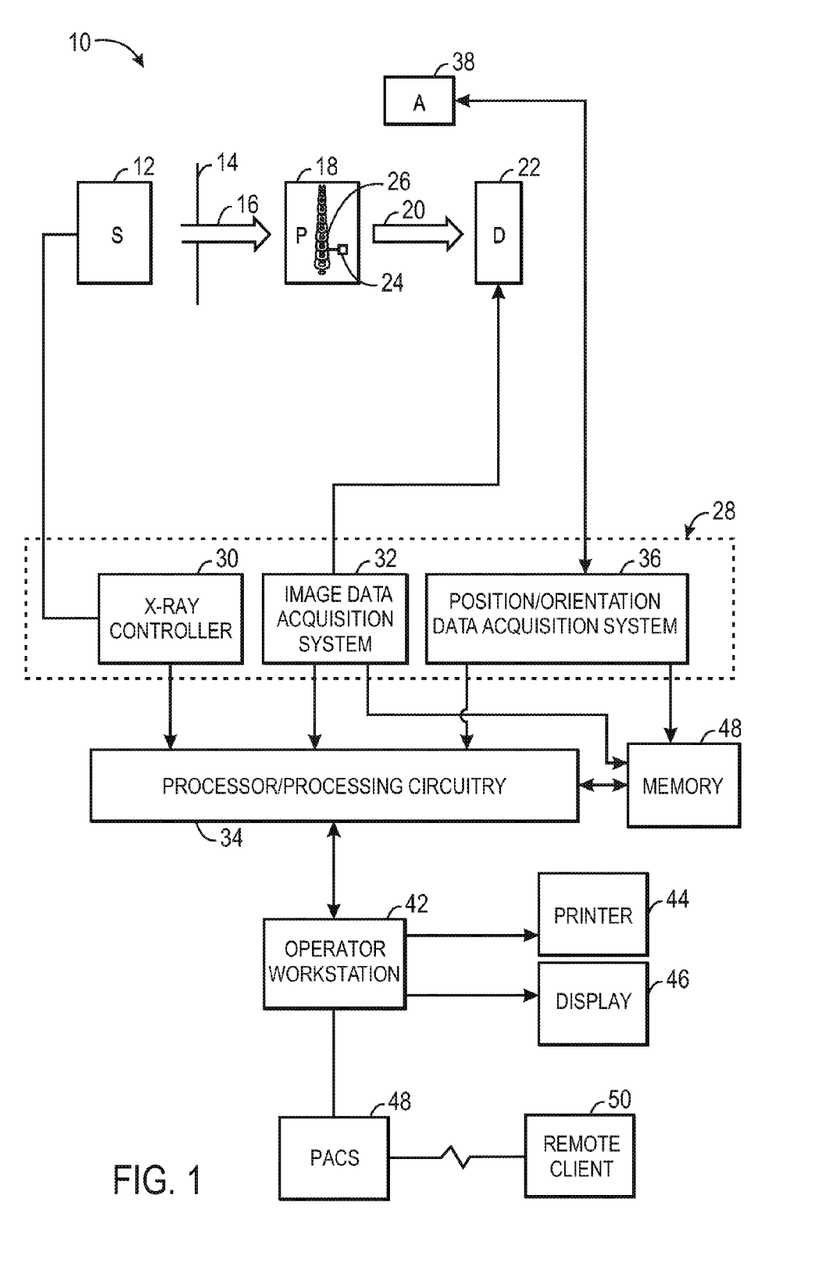
FIG. 1 depicts exemplary components of a fluoroscopy imaging system and a position determining system, in accordance with an exemplary embodiment of the present technique.

Moving now to the figures and referring initially to FIG. 1, a diagram of an X-ray based imaging system 10 for acquiring and registering fluoroscopic images and C-arm pose data is illustrated. In the illustrated embodiment, imaging system 10 is a fluoroscopy imaging system designed to acquire two-dimensional X-ray projection data and, in some embodiments, to process the image for mapping and registration in accordance with the present technique. In the embodiment illustrated in FIG. 1, X-ray based imaging system 10 includes a source of X-ray radiation 12 positioned adjacent to a collimator 14. The X-ray source 12 may be a standard X-ray tube or one or more solid-sate X-ray emitters.

In the depicted embodiment, the collimator 14 permits a stream of radiation 16 to pass into a region in which a subject, such as a patient 18 is positioned. During operation, a portion of the radiation 20 passes through or around the patient 18 and impacts a detector array, represented generally as reference numeral 22. Detector elements of the array produce electrical signals that represent the intensity of the incident X-ray beam. In some embodiments, the signals generated by the detector array 22 may be subsequently processed to generate image or positional data that may be used in conjunction with data generated by an EM sensor 24 secured within the patient 18. For example, tracked images of an anatomy of interest (e.g., a vertebral column) 26 may be registered and visualized in the depicted embodiment.

A variety of configurations of the detector 22 may be employed in conjunction with the techniques described herein. For example, the detector 22 may be an image-intensifier or an area detector (e.g., a flat-panel detector), such as a high-resolution radiographic detector having tens, hundreds, or thousands of rows and/or columns of detector elements, which allows positioning of the entire object or internal feature being imaged (such as vertebral column 26) within the field of view of the system 10. Regardless of the configuration, the detector 22 enables acquisition and/or measurement of image data used in the tracking and registration of the anatomy of interest 26.

The source 12 is controlled by a system controller 28, which furnishes both power and control signals for examination procedures. Moreover, the detector 22 is coupled to the system controller 28, which commands acquisition of the signals generated in the detector 22. The system controller 28 may also execute various signal processing and filtration functions, such as for initial adjustment of dynamic ranges, interleaving of digital image data, and so forth. In general, system controller 28 commands operation of the imaging system 10 to execute examination protocols and, in some embodiments, to process acquired data. In the present context, system controller 28 also includes signal processing circuitry, typically based upon a general purpose or application-specific digital computer, associated memory circuitry for storing programs and routines executed by the computer (such as programs and routines for implementing the present technique), as well as configuration parameters and image data, interface circuits, and so forth. Additionally, an X-ray controller 30 disposed within the system controller 28 may control the source 12 of radiation. Particularly, the X-ray controller 30 may be configured to provide power and timing signals to the X-ray source 12.

Further, the system controller 28 is also illustrated as including an image data acquisition system 32. In this embodiment, the detector 22 is coupled to the system controller 28, and more particularly to the image data acquisition system 32. The image data acquisition system 32 receives data collected by readout electronics of the detector 22. In one embodiment, the image data acquisition system 32 receives sampled analog signals from the detector 22 and converts the data to digital signals for subsequent processing by processing circuitry 34, which may, for example, be one or more processors of a general or application specific computer.

As depicted, the system controller 28 also includes a position/orientation data acquisition system 36 configured to acquire position and orientation data from one or more antennas 38. During operation, the one or more antennas 38 detect signals and/or fields generated by some or all of the EM sensor elements 24, 54 and 56 (depicted in FIG. 2). That is, the position/orientation data acquisition system 36 processes signals acquired from the antennas 38 to generate position and/or orientation information about the EM sensor 24 (and thus the anatomy of interest 26) as well as other EM sensors in proximity to the imaging system 10. The position and/or orientation information generated by the position/orientation data acquisition system 36 may be provided to the processing circuitry 34 and/or a memory 40 for subsequent processing. It should be understood that the antenna could either receive the signals/fields from the EM sensor elements or the antenna could generate the signals/field that are received by the EM sensor elements. Also, one of the EM sensor elements could take the place of the antenna.

The processing circuitry 34 is typically coupled to the system controller 28. The data collected by the image data acquisition system 32 and/or by the position/orientation data acquisition system 36 may be transmitted to the processing circuitry 34 for subsequent mapping of the EM sensor data to the fluoroscopic data. The processing circuitry 34 may include (or may communicate with) a memory 40 that can store data processed by the processing circuitry 34 or data to be processed (such as fluoroscopic images produced by the imaging of patient 18 or position/orientation data) by the processing circuitry 34. It should be understood that any type of computer accessible memory device capable of storing the desired amount of data and/or code may be utilized by the imaging system 10. Moreover, the memory 40 may include one or more memory devices, such as magnetic, solid state, or optical devices, of similar or different types, which may be local and/or remote to the system 10. The memory 40 may store data, processing parameters, and/or computer programs having one or more routines for performing the processes described herein.

The processing circuitry 34 may be adapted to control features enabled by the system controller 28, e.g., scanning operations and position/orientation data acquisition. For example, the processing circuitry 34 may be configured to receive commands and scanning parameters from an operator via an operator interface 42 typically equipped with, for example, a keyboard, mouse and/or other input devices. An operator may thereby control the system 10 via the input devices. A display 44 coupled to the operator interface 42 may be utilized to observe a tracked and registered 3D scan. Additionally, and image may be printed by a printer 46, which may be coupled to the operator interface 42. In some embodiments, one or more operator interfaces 42 may be linked to the system 10 for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

The processing circuitry 34 may also be coupled to a picture archiving and communications system (PACS) 48. Image data generated or processed by the processing circuitry 34 may be transmitted to and stored at the PACS 48 for subsequent processing or review. It should be noted that PACS 48 might be coupled to a remote client 50, radiology department information system (RIS), hospital information system (HIS) or to an internal or external network, so that others at different locations may gain access to the image data.

Figure 2:
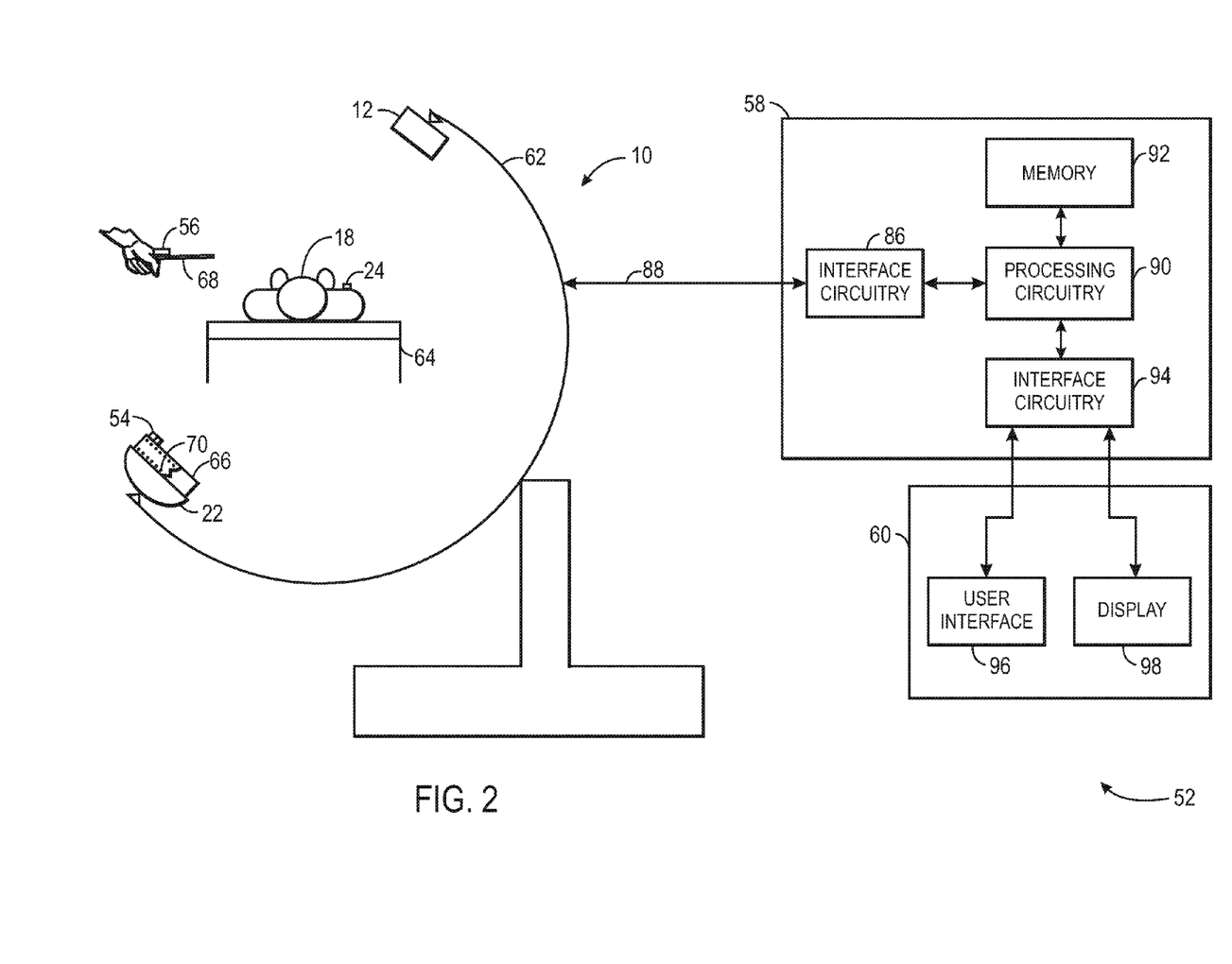
FIG. 2 is an illustration of an embodiment of a surgical navigation system in accordance with certain aspects of the present technique.

To discuss the technique in greater detail, a specific medical imaging modality based generally upon the overall system architecture outlined in FIG. 1 is depicted in FIG. 2, wherein a surgical navigation system 52 is illustrated. It may be appreciated that system 52 may contain features included in system 10 illustrated in FIG. 1. As such, those features are described using the same numerical reference. In the illustrated embodiment, navigation system 52 includes tracking components that include electromagnetic (EM) sensors 24, 54, and 56. Further, surgical navigation system 52 includes an X-ray imaging system 10 for acquiring and, in some embodiments, processing image data. As illustrated in this embodiment, surgical navigation system 52 further includes a computerized navigation system 58 and workstation 68.

X-ray imaging system 10 is illustrated as a C-arm fluoroscopy system that includes a C-arm 62, X-ray radiation source 12, and X-ray detector 22. The X-ray radiation source 12 is mounted on the C-arm 62, and the X-ray detector 22 is mounted on the C-arm 62 in an opposing location from the X-ray radiation source 12. While in some radiographic systems the X-ray radiation source 12 and the X-ray detector 22 may be fixed, in a typical fluoroscopy system the C-arm 62 allows for coordinated movement of the X-ray radiation source 12 and the X-ray detector 22 about the patient 18. In one embodiment, the X-ray radiation source 12 emits a stream of radiation 16 suitable for X-ray fluoroscopy. The X-ray detector 22 receives a portion the stream of radiation 20 from the X-ray source 12 that passes through the patient 18 positioned on a table 64. The X-ray detector 22 produces electrical signals that represent the intensity of the radiation stream. As those of ordinary skill in the art will appreciate, these signals are suitably acquired and processed to track and subsequently image features within the subject.

A plurality of EM sensors may be fixed in relation to the fluoroscopy system. In the illustrated embodiment, EM sensor 54 is fixed to a calibration assembly 66, which is fixed on the X-ray detector 22 of the X-ray imaging system 10. As illustrated, the EM sensor 24 is fixed on the patient 18, though it should be noted that EM sensor 24 may be fixed within the patient 18, for example, to an internal structure 26 of interest, such as a skeletal feature. EM sensor 56 may be fixed in relation to a medical (e.g., surgical) device 68. In the illustrated embodiment, the EM sensor 56 is mounted on the operative end of the medical device 68. Device 68 may be may be any suitable device for use in a medical procedure. For example, device 68 may be a pointer, a drill, a guide wire, a catheter, an endoscope, a laparoscope, a biopsy needle, an ablation device or other similar devices.

The calibration assembly 66 may include radiopaque markers 70 fixed within a radiolucent material. In some embodiments, the calibration assembly 66 may be considered a calibration target, as the assembly 66 is positioned on the X-ray detector 22 such that at least a portion of the markers 70 within the assembly 66 are visible in every fluoroscopic image. During operation, the markers 70 of the calibration assembly 66 may be tracked via the EM sensor 54, such that the position of each marker 70 is known in every fluoroscopic image. The radiopaque markers 70 are usually fixed in relation to one another, such that their respective positions may be used to provide an accurate reference between the coordinate frames of EM sensors 24, 54 and 56 and each 2D fluoroscopic image. Further, the markers' geometry is used to model the source and detector projection geometry. That is, the position of the markers 70 within each fluoroscopic image may allow an operator to determine the perspective from which the fluoroscopic image was taken (i.e. the position of the C-arm 62 with respect to the patient 18). The resultant model used for such geometric determinations is often referred to as a perspective projection model or a projection model.

In a general sense, the EM sensors 24, 54 and 56 may be implemented as non-optical EM receivers or non-optical EM transmitters, i.e., as EM components that transmit and/or receive using portions of the EM spectrum that do not correspond to optical or visible light. For example, in some applications of the present technique, the EM sensors 24, 54 and 56 may employ the radiofrequency (RF) portion of the electromagnetic spectrum and have a working range of between about 3 inches to about 18 inches. In one embodiment, EM sensor 24 may be implemented as an EM transmitter, while the remaining EM sensors 54 and 56 may be implemented as EM receivers. In such an embodiment, the signals sensed by EM sensor 56 that is fixed in relation to the device 68 may be used to determine the spatial properties of the device 68, for example, the position (e.g., the X-, Y-, and Z-coordinates) and orientation (e.g., the pitch, yaw, and roll angles). As will be appreciated, the mutual inductance of two EM sensors is the same, regardless as to which is the receiver and the transmitter. Therefore, relative positioning and functionality of the EM receivers and transmitters may be reversed. For example, the EM sensor 24 that is fixed in relation to the patient may be implemented as an EM receiver, while the remaining EM sensors 54 and 56 may be implemented as EM transmitters. Likewise, any other suitable combination of EM transmitters and receivers may be implemented as the EM sensors 24, 54, and 56.

In some embodiments, each of the EM sensors 24, 54 and 56 may contain materials (e.g., coils, current loops, electromagnets, etc.) capable of producing a dipole magnetic field when a current is applied to or induced through them. Electromagnetic fields generated by each of the dipoles are distinguishable from one another in phase, frequency, time division multiplexing, and the like. The near-field characteristics of the electromagnetic fields may be used to determine spatial properties, such as position coordinates and/or orientation information. In some embodiments, one or more of the EM sensors 24, 54 and 56 may employ industry-standard coil architecture (ISCA) type coils, a single dipole coil, or a combination thereof. ISCA coils generally may be defined as three, approximately collocated, approximately orthogonal, and approximately dipole coils. Alternatively, one or more of the EM sensors 24, 54 and 56 may be configured with a single coil that generates a single dipole magnetic field. In addition, one or more of the EM sensors 24, 54 and 56 may employ technologies other than a coil, including, for example, Hall Effect, magnetoresistance, or flux gate devices. In certain embodiments, the EM sensors 24, 54 and 56 may operate in a wired or wireless configuration.

Further, the EM sensors 24, 54 and 56 may have enclosures made of materials that allow electromagnetic information to be transmitted and sensed through the material in a substantially undistorted manner. Such materials may include biocompatible plastics for patient use, and any other suitable plastics for attachment to equipment such as the detector 22 and medical device 68. The enclosure of EM sensor 24 may also have features for attaching the EM sensor 24 to hard patient anatomy (i.e. bone), such as a screw. It may be appreciated that EM sensor 24 should be of a size that allows a significant freedom in the method and/or location of attachment while allowing the anatomy 26 to be moved if necessary. For example, in one embodiment EM sensor 24 may have a generally cubic configuration, and may be about 1 cm$^3$. In some embodiments, the anatomy of interest 26 within the patient 18 may be in an area where space is limited. To provide for such instances, the EM sensor 24 (or any sensor used according to the present technique) may employ microcoils, allowing the EM sensors to have generally flat configurations. In one example, the EM sensor 24 is an RFID-like sensor that can be attached within the patient 18. In such an instance, the microcoils may be dimensioned such that it may be necessary to dispose multiple EM sensors within the patient 18. For example, a relatively flat RFID-like sensor may have microcoils aligned such that not all six degrees of freedom are sensed. As such, multiple RFID-like sensors may ensure that the sensing of all 6 positional elements (X-, Y-, and Z-coordinates, roll, pitch, and yaw) is maintained. In these aspects of the present technique where RFID-like sensing elements are used, direct attachment to, and thus positional sensing of, soft tissues may be afforded.

Figure 3:
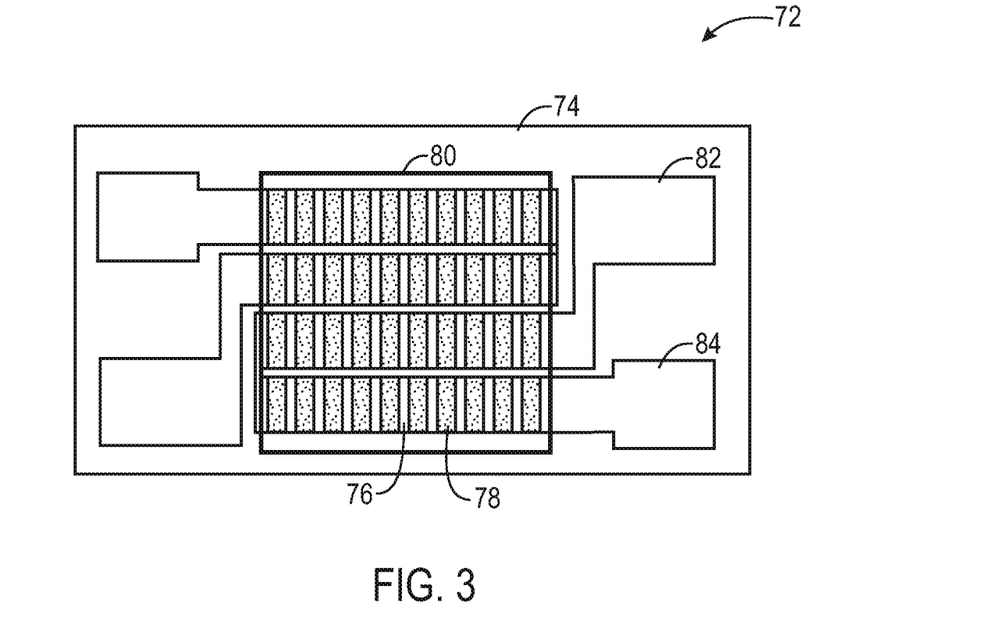
FIG. 3 is an enlarged top view of an embodiment of a magnetoresistance sensor in accordance with the present technique.
Figure 4:
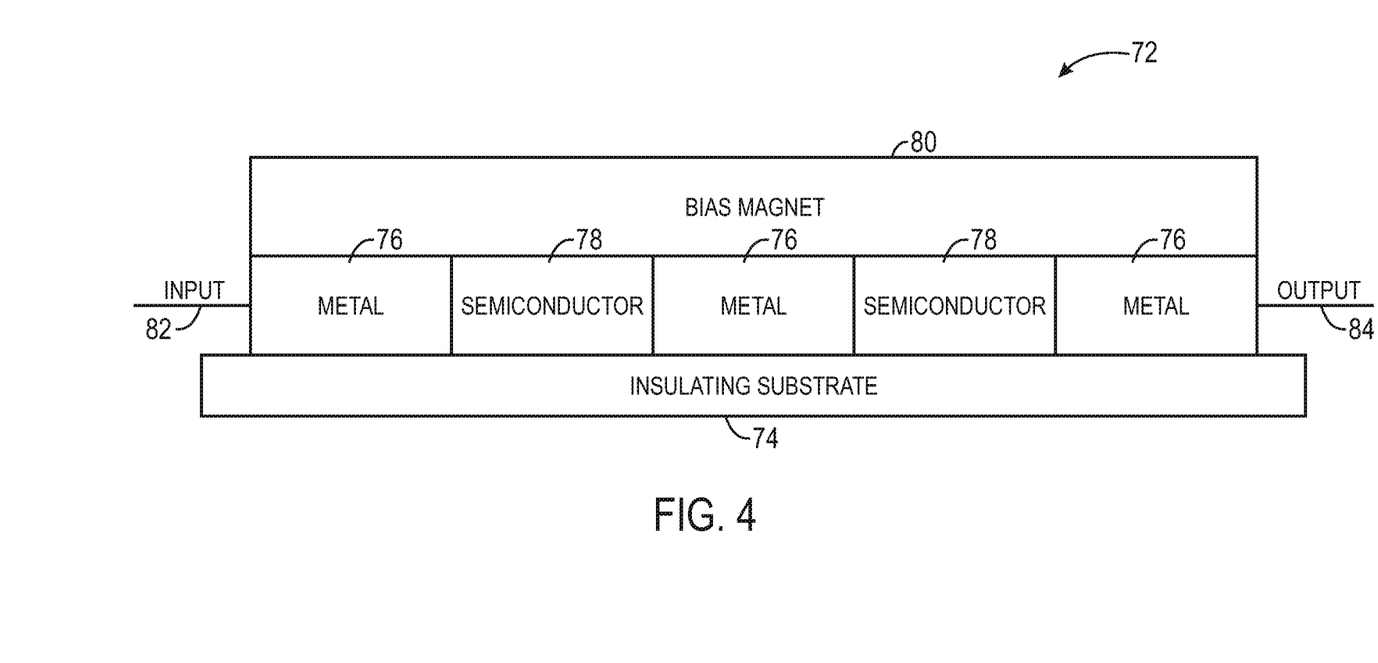
FIG. 4 is an enlarged side view of an embodiment of a magnetoresistance sensor in accordance with the present technique.

In one embodiment according to the present technique, EM sensors 24, 54, and 56 may be implemented as a magnetoresistant sensor 72, an embodiment of which is illustrated in a top-down and a side-on view in FIGS. 3 and 4, respectively. In the illustrated embodiment, the device 72 provides a change in electrical resistance of a conductor or semiconductor when a magnetic field is applied. In such an embodiment, the device's resistance depends upon the magnetic field applied. As shown in FIGS. 3 and 4, the magnetoresistance sensor 72 generally includes an insulating substrate 74, an alternating pattern of a metal material 76 and a semiconductor material 78 deposited on the insulating substrate 74, as well a bias magnet material 80 deposited over the alternating pattern of metal material 76 and semiconductor material 78. The magnetoresistance sensor 72 may also include an input connection contact 82 and an output connection contact 84. As illustrated in FIG. 4, the alternating pattern of metal material 76 and semiconductor material 78 creates a composite structure. At least one of the input connection contacts 82 is coupled to the metal material 76 and at least one of the output connection contacts 84 is coupled to the metal material 76 to allow a flow of electrons through the sensor 72.

The semiconductor material 78 may be series connected to increase the resistance of the magnetoresistance sensor 72. In one particular embodiment, the semiconductor material 78 may contain a single semiconductor element. In operation, the bias magnet material 80 subjects the semiconductor material 78 to a magnetic field required to achieve a required sensitivity. The magnetoresistance sensor 72 provides a signal in response to the strength and direction of a magnetic field. The magnetic field may be approximately 0.1 to 0.2 Tesla. In one embodiment, the application of a magnetic field confines the electrons flowing through the sensor 72 to the semiconductor material 78, resulting in an increased path length, which may increase the sensitivity of the magnetoresistance sensor 72. The magnetic field may also increase the resistance of the magnetoresistance sensor 72. In the geometry illustrated in FIGS. 3 and 4, at a magnetic field of zero, the current density is substantially uniform throughout the magnetoresistance sensor 72. At a high magnetic field, the electrons (or holes) propagate radially outward toward the corners of the semiconductor material 78, resulting in a large magnetoresistance (high resistance).

In one embodiment according to the present technique, the magnetoresistance sensor may be built with various architectures and geometries, including giant magnetoresistance (GMR) sensors, and extraordinary magnetoresistance (EMR) sensors. The magnetoresistance sensor 72 may provide a very small form factor, excellent signal-to-noise ratio (low noise operation), and excellent low frequency response. Low noise combined with wide dynamic range enables the magnetoresistance sensor 72 to be used for position and orientation tracking according to the present technique, such as within the patient 18 or on the device 68. The low frequency response of the magnetoresistance sensor 72 may allow the position and orientation tracking system 36 to operate at very low frequencies where metal tolerance is maximized (i.e., in the presence of the C-arm 62).

Returning to FIG. 2, as previously mentioned, the surgical navigation system 52 may further include computerized navigation system 58. In the illustrated embodiment, computerized navigation system 58 includes interface circuitry 86 for receiving tracking and imaging data, represented generally by arrow 88. In some embodiments, some or all of the tracking and imaging data 88 that is sent to the computerized navigation system 58 has been processed and analyzed by the processing circuitry 34 and memory 48 of imaging system 10. The computerized navigation system 58 may also include processing circuitry 90, memory unit 92, and workstation interface circuitry 94. As will be appreciated, one or more computers may be used to implement computerized navigation system 58. In general, processing circuitry 90, which may typically include a digital signal processor, a CPU or the like, may process the tracking data so that the location of the device 68 may be tracked, mapped and registered to a pre-operative 3D scan. Memory unit 92 may serve to save the imaging and tracking data as well as other system parameters. In some embodiments, the memory unit 92 may be any computer-readable medium such as an optical media (e.g., compact discs, digital video discs), a solid-state memory device (USB drive, flash drive), a hard drive, a memory card, and the like. In one embodiment, the memory unit 92 contains computer code that is executed by the processing circuitry 90. The workstation interface circuitry 94 may be configured for communicating with workstation 68.

As illustrated, the surgical navigation system 52 further includes the workstation 68, which includes a user interface 96 and a display 98, which may or may not correspond to operator interface 42 and display 44 depicted in FIG. 1. The user interface 96 may include a keyboard and/or mouse, as well as other devices such as printers or other peripherals for reproducing hardcopies of the reconstructed images. Display 98 may include one or more screens. For example, the display 98 may include a first screen for displaying a previously acquired image and a second screen for displaying one or more intra-operative images.

The systems and devices described above may be utilized, as described herein, to provide dynamic referencing for a region of a patient undergoing an interventional or surgical procedure. In one embodiment utilizing the present technique, dynamically acquired position and orientation data for the region of the patient may be acquired using the EM sensor elements 24, 54 and 56, the data then may be automatically mapped with concurrently acquired 2D fluoroscopic image data followed by registry to a pre-operative 3D scan. In this way, the interventional or surgical procedure may be performed or guided based upon the dynamically referenced visual representation of the pre-operative 3D scan.

Figure 5:
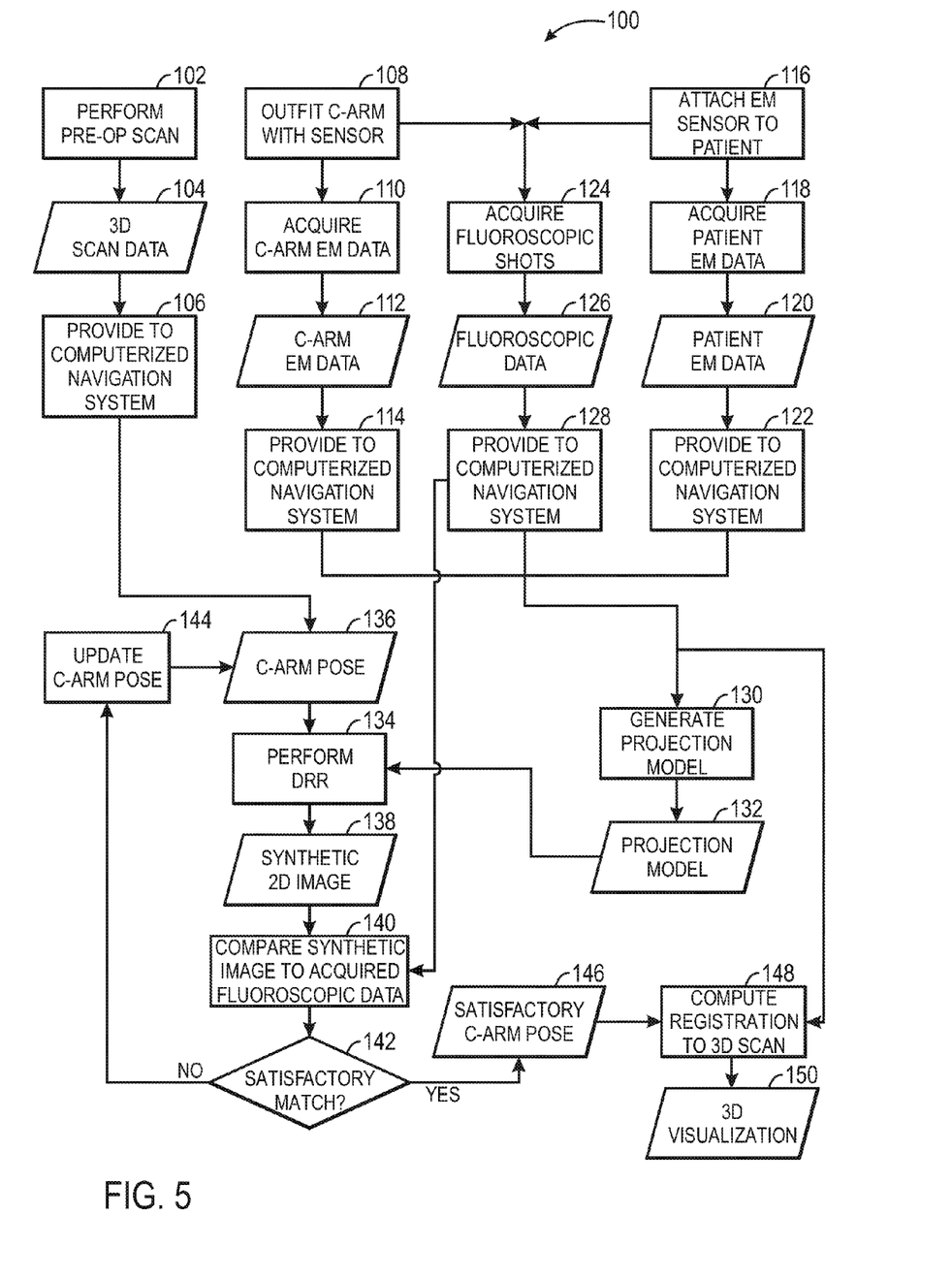
FIG. 5 is a flowchart depicting an embodiment of a general method for registering intra-operative fluoroscopic scans of a patient to a pre-operative 3D scan in accordance with certain aspects of the present technique.

Referring now to FIG. 5, an example method 100 for using the surgical navigation system 52 to monitor the patient 18 by registering two or more planar fluoroscopic images to a 3D scan is depicted in flowchart form. As depicted at block 102, a pre-operative 3D scan may be performed on the patient 18. The pre-operative scan may be performed using a CT, PET, MRI, SPECT, or similar 3D imaging modality. The 3D scan data 104 is then provided to a computerized navigation system 58 for subsequent processing (block 106).

As depicted at block 108, the method may include providing a navigated (tracked) X-ray imaging system 10, such as a fluoroscopy system mounted on a C-arm. The C-arm 62 may be fitted with an EM sensor 54, as discussed herein. The C-arm 62 also includes the calibration target 66 which may aid in establishing the relative position of the C-arm 62 fluoroscopic image with respect to EM sensors 24 and 56. The C-arm EM signal is acquired (block 110) for example, by antennas 38 or other EM devices. The C-arm EM data 112 is then provided to the computerized navigation system 58, in accordance with block 114. In some embodiments, during operation of the surgical navigation system 52 the EM field around the C-arm 62 may become distorted by the metal of the C-arm 62 or other interference sources. The computerized navigation system 58 may offset this distortion by mapping the distorted to undistorted space and performing a correction function using, for example, a high order polynomial fitting.

As depicted at block 116, the patient 18 may be prepared for the interventional procedure by, for example, attaching one or more EM sensors (such as EM sensor 24) to the patient 18. In some embodiments, the EM sensor 24 may be attached to patient bone. In one embodiment, the EM sensor 24 is attached to a portion of the vertebral column. In some embodiments, the attachment may be performed percutaneously. That is, the attachment may be relatively non-invasive. Conversely, in some embodiments, the attachment may be performed as apart of an invasive procedure, where the anatomy of interest 26 is exposed. In certain of these embodiments, there may be multiple EM sensors that are secured (e.g., via an adhesive) to a soft tissue area. In these embodiments, patient preparation may also include injection of a contrast agent into the bloodstream of the patient 18. Nevertheless, securing the EM sensor 24 to the patient 18 should allow the patient to move while providing accurate navigation. For example, the EM sensor 24 may generate a tracking signal such as a magnetic field that is responsive to the position of the anatomy of interest 26. As previously mentioned, in certain embodiments, the reference EM sensor 24 may be the sensor 72 described in FIGS. 3 and 4. The patient (reference) EM signal is acquired (block 118) for example, by antennas 38 or other EM devices. The patient EM data 120 is then provided (block 122) to the computerized navigation system 58.

In accordance with a further aspect of the present technique, the method provides, as depicted at block 124, the step of acquiring at least two initial fluoroscopic images of the patient 18 using the navigated X-ray imaging system 10. In one embodiment, the fluoroscopic images provide fluoroscopic data 126 of an area surrounding the anatomy of interest 26. For example, two different X-ray projections of a portion of the vertebral column may be taken from different angular positions (e.g., anterior/posterior and lateral) relative to the patient. In another example, two similar positional images (anterior/posterior and lateral) may be acquired for an area of soft tissue or blood vessels (e.g., blood vessels to which a contrast agent has been provided).

The data, including the EM positional data 112 and 120, in addition to the fluoroscopic data 126, may be provided to the computerized navigation system 58 as raw data, in addition to or in lieu of a video capture. Thus, the computerized navigation system 58 may perform various transforms and algorithms on raw rather than reconstructed data sets, which may serve to increase computational efficiency. In some embodiments, the increased computational efficiency may enable the surgical navigation system 52 to operate in a substantially real time configuration. Accordingly, the fluoroscopic data 126 is provided (block 128) to the computerized navigation system 58.

In some embodiments, the fluoroscopic data 126 that is generated using the C-arm 62 may be processed to map the 2D fluoroscopic data 126 (e.g., 2D fluoroscopic projection images) to the 3D space that is generated by the EM sensors 24 and 54 using the calibration target 66. That is, in some embodiments, the computerized navigation system 58 may generate (block 130) a perspective projection model 132 such that a 3D point in the tracked space can be correlated to a 2D pixel of the fluoroscopic data (e.g., image) 126. In these embodiments, the position of the radiopaque markers 70 of the calibration assembly 66 within the fluoroscopic image 126 serves to establish a perspective projection plane for each fluoroscopic image taken. In other words, the calibration target 66 serves to represent the position of the C-arm 62 in relation to the patient 18 by allowing an operator to relate the position of the sensed positional trackers (EM sensors 24, 54 and 56) to the fluoroscopic images 126. Further, establishing a perspective projection plane may ease the process of registration, as the computerized navigation system 58 may only have to process a limited number of position and orientation possibilities for the patient 18 to match the fluoroscopic images 126 to the 3D scan data 104. That is, the projection model 132 may constrain the nearly infinite number of orientation and position possibilities to a well-defined set having a high probability for matching. The projection model 132 may also serve to aid in image distortion correction. For example, in some embodiments where the fluoroscopic image 126 is geometrically distorted through use of a curved image intensifier, the computerized navigation system 58 may perform a correction function using the projection model 132.

Once the projection model 132 has been established, the computerized navigation system 58 may begin a digital radiographic reconstruction (DRR) 134 for the eventual registration of the fluoroscopic data 126 to the initial 3D scan data 104. To begin DRR 134, an input is provided from the computerized navigation system 58 (e.g., input from a human operator) as to a calculated pose 136 (position and orientation) of the C-arm 62 with respect to the 3D scan 104. The computerized navigation system 58 uses DRR 134 to generate synthetic 2-dimensional projections 138 of the 3D scan 104 from the calculated pose 136. In some embodiments, the synthetic 2D images 138 may equal the number of fluoroscopic images 126 acquired in step 124. In a subsequent step 140, each of the synthetic images 138 is matched and compared to a fluoroscopic image 126 using the projection model 132 for each image 126 using algorithms such as mutual information-based algorithms, edge-detection algorithms, and the like. The comparison may be based on an accuracy metric designed to ascertain the relative match between the synthetic image 138 and the acquired fluoroscopic images 126. It should be noted that the matching and comparison 140 may or may not be on a pixel-by-pixel basis. For example, matching and comparison 140 may be performed on areas of the images 138, 126 rather than on individual pixels. In step 142, a query is performed as to whether the synthetic images 138 are a satisfactory match to the acquired fluoroscopic images 126. If a satisfactory match is not obtained, method 100 may cycle to a step 144, where the calculated C-arm pose 136 is updated. Of course, the steps of performing DRR 134, matching and comparison 140, and updating the C-arm pose 144 may be reiterated until a satisfactory pose 146 is obtained. Further, it should be noted that these steps are done for each pair of synthetic image 138 and fluoroscopic image 126, with the number of synthetic images 138 equaling the number of the at least 2 fluoroscopic images acquired in step 124. Once the satisfactory pose 146 has been obtained, it is used, along with the C-arm EM data 112, the fluoroscopic images 126, and the patient EM data 120 to compute registration of the patient 18 to the 3D scan 104 in a step 148, the output of which is a substantially real-time 3D visualization 150 of the patient 18 and the anatomy of interest 26.

Figure 6:
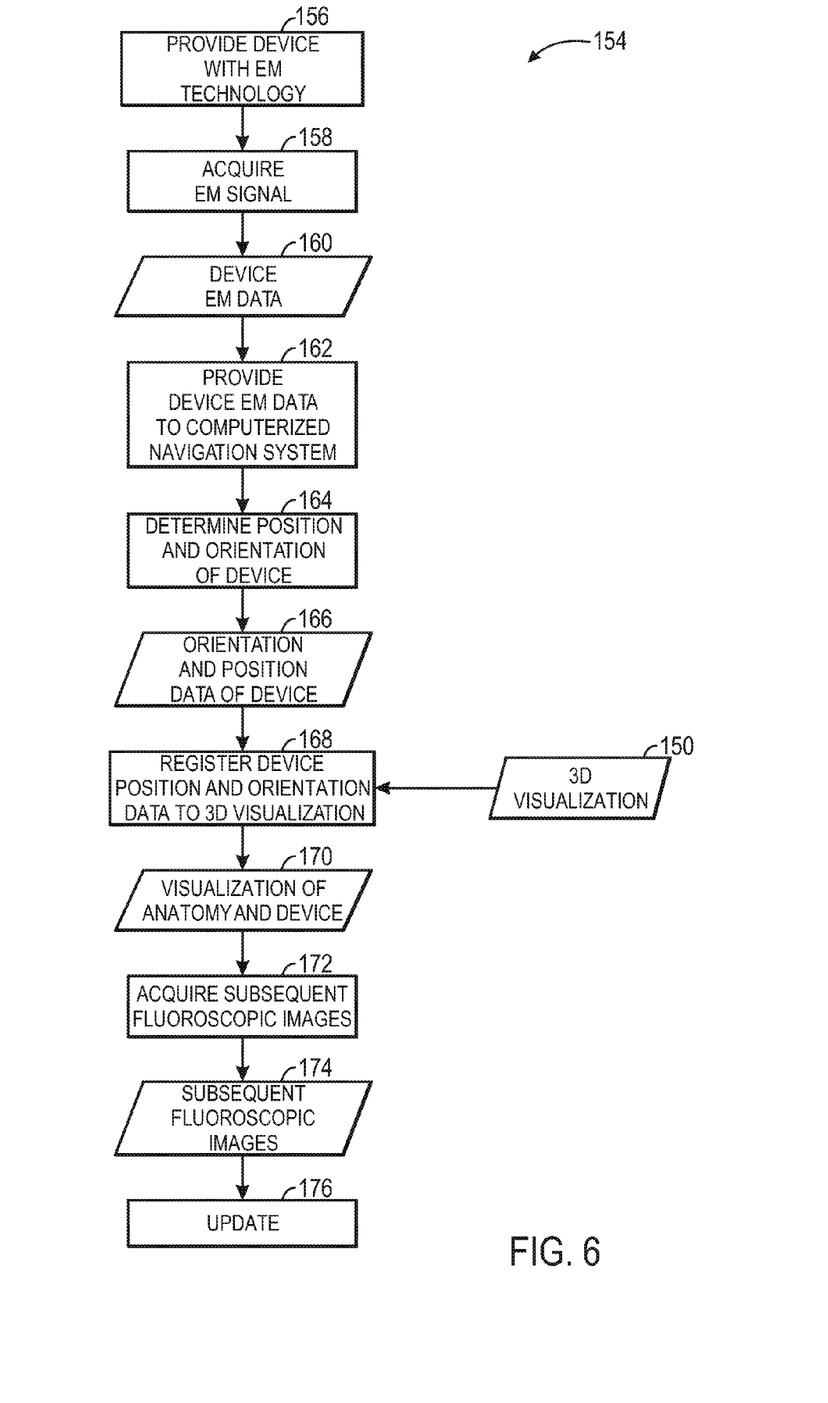
FIG. 6 is a flowchart depicting embodiments of a general method for tracking a medical device during a navigated surgical procedure, in accordance with certain aspects of the present technique.

This allows an operator, such as a surgeon, to interactively monitor the patient anatomy of interest 26 based on an updated 3D anatomy visualization 150, such as a CT scan, using the fluoroscopic images 126 produced by the fluoroscope system 10. In embodiments where the monitoring of the patient 18 is part of a surgical procedure, the computerized navigation system 58 may allow registration of a surgical instrument, such as the medical device 68. To allow proper positioning and manipulation of the device 68 within the patient 18, it may be desirable to provide methods for tracking and registration of the device 68 in the context of the 3D visualization 150. With the foregoing methods in mind, the current technique also provides, as shown in FIG. 6, a method 154 for performing an interventional or surgical procedure by tracking the medical device 68 in relation to patient anatomy 26 and updating the position of the device 68. In the depicted embodiment, as with method 100, the operator, such as a surgeon, may be able to interactively monitor the procedure based on updating a 3D visualization.

Thus, as depicted at block 156, the method may include an operator (e.g., a physician) providing the device 68 with EM sensor 56 attached. The sensor 56 may transmit a tracking signal, for example, a signal representative of the device 68. As with the EM sensors 24 and 54, the EM sensor 56 on the device 68 may generate a magnetic field that is responsive to the position of the device 68. As previously mentioned, in certain embodiments, the EM sensor 56 may include a single dipole coil that is provided a drive current to generate a magnetic field having a given magnitude, phase and frequency.

As depicted at block 158, the method further may include acquiring the tracking signal of the EM sensor 56. In one embodiment, the tracking signal may be received by one or more antennas 38. In certain of these embodiments, the tracking signal generated by the device EM sensor 56 may be affected by external sources. For example, a signal (e.g., a magnetic field) from the patient EM sensor 24 may be received by the device EM sensor 56. In such an embodiment, the EM signal generated by the patient EM sensor 24 may induce a current across the device EM sensor 56, such as across one or more coils in the device EM sensor 56. The induced current may cause anisotropy in the device's tracking signal, such that the tracking signal is representative of positional aspects of the device 68 with respect to the patient 18. Of course, if the orientation of the coils within the device 68 is known with respect to the orientation of the device 68, the anisotropic EM signal may also indicate the device's orientation (e.g., where the tip of the device is located). The EM data 160 may be processed, for example, to determine position and orientation information. The EM data 156 may be provided (block 162) to the computerized navigation system 58.

According to a block 164, the method further includes determining the position and orientation of the device 68. As mentioned, the tracking signal produced by the patient EM sensor 24 and received by the device EM sensor 56 may be used to determine the position and orientation of the EM sensor 56 affixed to the device 68. The tracked position and orientation of the EM sensor 56 may then be used to determine the position and orientation of the device 68, such as the tip of the device 68. In these embodiments, the computerized navigation system 58 may produce orientation and position data 166 of the device 68.

In some embodiments, the device's position and orientation data 166 may be directly registered (block 168) to the 3D anatomy visualization 150. Upon registering the device 68 to the 3D anatomy visualization 150, the computerized navigation system 58 may produce a combined 3D visualization 170 of the tracked device in the context of the anatomy. For example, the combined visualization 170 may have an image or an icon representing the device 68 displayed with reference to or in the context of the patient anatomy as depicted in the 3D anatomy visualization 150.

The operator of the device 68 should be able to use the combined visualization 170 of the device 68 in the context of the 3D scan to assist in the manipulation of the device 68 within the patient 18. For example, the combined visualization 170 of the device 68 may assist the operator in the precise and rapid positioning of the device 68 within the patient 18. In some embodiments, the combined 3D visualization 170 of the positioning of the device 68 within the patient 18 may be displayed from a variety of perspectives relative to the device 68. For example, the positioning of the tip of the device 68 within the patient 18 may be displayed from sectional planes of the patient 18, such as coronal, sagittal, and/or transverse planes or in the context of a volume rendering. In some embodiments, the position of the device 68 relative to the patient anatomy 26 may be updated by acquiring subsequent fluoroscopic images 174 (e.g. one or two images) and updating (block 176) as appropriate. For example, re-registry of the patient 18 may be performed, such as computed registration 148 in method 100, creating a new updated 3D anatomy visualization 150. In such an embodiment, it may be appreciated that the method 154 may be performed each time re-registration of the patient 18 is performed. Despite this, in one embodiment, method 154 and method 100 may be performed substantially concurrently. For example, the acquisition of the EM signals according to blocks 110, 118 and 158 may occur at about the same time. The computerized navigation system 58 may then perform the remainder of the steps of methods 154 and 100 in parallel, such that DRR (block 134) is performed at about the same time as the registration of the device (block 168). In these aspects, the 3D patient visualization 150 may be the same as the combined 3D visualization of the patient and device 170.

Figure 7:
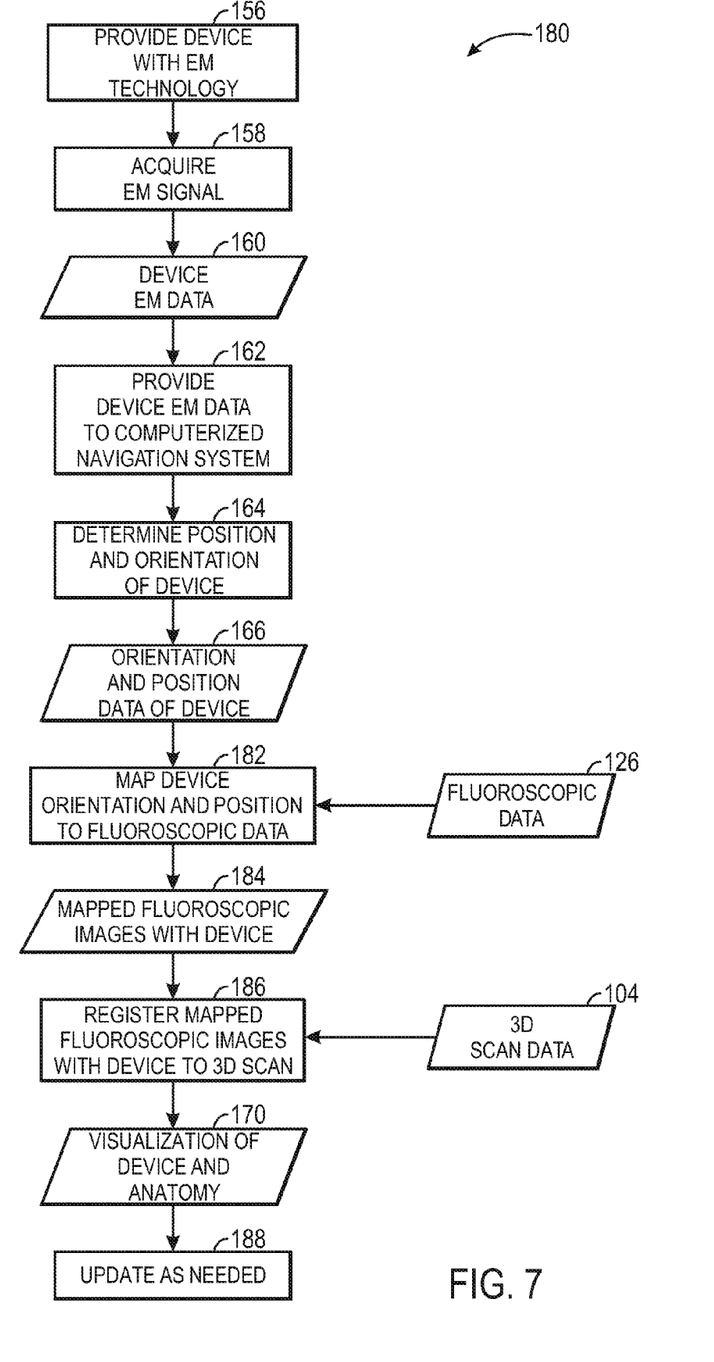
FIG. 7 is a flowchart depicting an embodiment of a method for tracking a medical device during a navigated surgical procedure, in accordance with an aspect of the current technique.

The present technique may also provide a method 180, as illustrated in FIG. 7, of performing a navigated interventional procedure by mapping the orientation and position data 166 of the device 68 to the initial fluoroscopic images 126. It may be appreciated that the method 180 may include performing similar tasks described in method 154. As such, those tasks are described using similar reference numerals. Thus, the device 68 fitted with the EM sensor 56 may be provided (block 156). The EM signal 160 of device 68 may be acquired (block 158) by, for example, antennas 38. The device EM data 156 may then be provided (block 162) to the computerized navigation system 58. According to block 164, the position and orientation information 166 may be produced.

In an embodiment, the method 180 includes, as depicted by block 182, mapping the position and orientation data 138 of the device 68 to the initial fluoroscopic images 126, such as two initial fluoroscopic images. By way of example, an icon or image representing the device 68 (or the device tip) position and orientation may be mapped onto the fluoroscopic images 126 to produce a mapped fluoroscopic image 184 with a device representation. The mapped fluoroscopic images 184 may then be registered (block 186) to the pre-operative 3D scan 104 or, in other embodiments, the 3D anatomy visualization 136. The computerized navigation system 58 may then produce the combined visualization 170 of the device 68 and patient anatomy 26 in a tracked and updated 3D scan. The combined visualization 170 may be updated (block 188) to track the position of the device 68 with respect to the patient 18.

In some embodiments, by performing tracking of the device 68 according to the techniques in method 180, the method 180 and the method 100 may be performed substantially concurrently. For example, the step according to blocks 110 and 118 in method 100, where the EM data from the C-arm 62 and patient 18 is acquired, respectively, may occur substantially concurrently with the acts associated with block 158 (acquiring the EM signal of the device) of method 180. Additionally, the computerized navigation system 58 may perform mapping of the device orientation and position data 166 to the two initial fluoroscopic images 126 according to block 182 to generate the device-mapped fluoroscopic scan 184 substantially concurrently with generation of the projection model (block 130). Indeed, in one embodiment, the projection model 132 accounts for the device orientation and position data 138, such that the monitoring of the patient anatomy of interest 26 and the monitoring the device 68 is a single process (a combination of methods 100 and 180).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A surgical navigation method comprising the acts of:
   establishing a coordinate frame by fixing a first electromagnetic device to a patient;
   acquiring two or more two-dimensional fluoroscopic images of the patient each from a different perspective using an imaging apparatus, the imaging apparatus comprising a source of X-ray radiation and an X-ray detector having a second electromagnetic device and a calibration target affixed thereto, and wherein the calibration target comprises a series of radiopaque markers that are fixed in relation to one another;
   modeling a geometry of the source of X-ray radiation and the X-ray detector based at least on a geometry of the radiopaque markers in each two-dimensional fluoroscopic image to obtain a perspective from which each image was taken;
   providing a pre-operative three-dimensional image, the two or more two-dimensional fluoroscopic images, tracking data representing a position and orientation of the second electromagnetic device with respect to the first electromagnetic device, and the perspective from which each two-dimensional fluoroscopic image was taken to a computerized navigation system;

generating a respective two-dimensional projection via digital radiographic reconstruction (DRR) of the pre-operative three-dimensional image using the perspective from which each two-dimensional fluoroscopic image was taken and an input pose of the imaging apparatus relative to the pre-operative three-dimensional image;

comparing the generated two-dimensional projections to the acquired two or more two-dimensional fluoroscopic images;

updating the input pose based on the comparison to generate updated projections via DRR until the updated projections meet a predetermined matching criteria with the acquired two or more two-dimensional fluoroscopic images, the predetermined criteria being a result of a registration pose; and generating a substantially real-time three-dimensional visualization of the patient based on the registration pose and the pre-operative three-dimensional image.

2. The method of claim 1, wherein the comparison between the generated two-dimensional projections and the acquired two or more two-dimensional fluoroscopic images is performed on a pixel-by-pixel basis.

3. The method of claim 1, wherein at least two of the two or more two-dimensional fluoroscopic images are taken from perspectives that are angled relative to one another.

4. The method of claim 1, wherein the first electromagnetic device does not comprise an optical sensor or marker.

5. The method of claim 1, wherein the first electromagnetic device is disposed on or within the patient percutaneously.

6. The method of claim 1, wherein the first electromagnetic device is attached to a bone of the patient.

7. The method of claim 1, wherein the three-dimensional representation comprises a CT scan.

8. The method of claim 1, wherein the two or more two-dimensional fluoroscopic images are acquired using a C-arm imager.

9. The method of claim 1, wherein the two or more two-dimensional fluoroscopic images comprise two, three, or four two-dimensional fluoroscopic images.

10. A method of surgical navigation comprising the acts of:
attaching a first electromagnetic device to a patient anatomy of interest to establish a coordinate frame;

performing an acquisition of two or more two-dimensional fluoroscopic images using a C-arm imaging system, wherein the C-arm imaging system comprises a second electromagnetic device and a calibration target;

performing a registration operation using a computerized navigation system configured to process the coordinate frame, the two or more two-dimensional fluoroscopic images, a projection model generated using calibration data derived based upon the calibration target and spatial data derived for the C-arm using the second electromagnetic device, digital radiographic reconstruction (DRR) images generated using the projection model and a calculated pose of the C-arm imaging system relative to a three-dimensional representation of the patient anatomy of interest generated prior to surgery, and the three-dimensional representation of the patient anatomy of interest generated prior to surgery, wherein the registration operation generates a three-dimensional visualization of the patient; and monitoring a representation of a surgical tool depicted with respect to the three-dimensional visualization, wherein the surgical tool is equipped with a third electromagnetic device.

11. The method of claim 10, comprising:
acquiring additional two-dimensional fluoroscopic images after the three-dimensional visualization is generated; and updating the registration and the three-dimensional visualization based on the additional two-dimensional fluoroscopic images.

12. The method of claim 10, wherein the two or more two-dimensional fluoroscopic images are taken from perspectives that are angled relative to one another.

13. The method of claim 10, wherein the first, second and third electromagnetic devices generate a signal representative of a position and orientation of the patient, the C-arm imaging system, and the medical device, respectively.

14. The method of claim 10, further comprising viewing the 3D visualization of the device and the patient from a coronal, sagittal, or axial plane perspective of the patient.

* * * * *